US011752166B2

(12) United States Patent
Jacobson et al.

(10) Patent No.: US 11,752,166 B2
(45) Date of Patent: Sep. 12, 2023

(54) COMBINATION THERAPY FOR TREATMENT OF HCV

(71) Applicant: COCRYSTAL PHARMA, INC., Bothell, WA (US)

(72) Inventors: Irina C. Jacobson, Sammamish, WA (US); Biing Yuan Lin, Bellevue, WA (US); Sam SK Lee, Edmonds, WA (US)

(73) Assignee: COCRYSTAL PHARMA, INC., Bothell, WA (US)

( * ) Notice: Subject to any disclaimer, the term of this patent is extended or adjusted under 35 U.S.C. 154(b) by 66 days.

(21) Appl. No.: 17/047,209

(22) PCT Filed: May 9, 2019

(86) PCT No.: PCT/US2019/031459
§ 371 (c)(1),
(2) Date: Oct. 13, 2020

(87) PCT Pub. No.: WO2019/217643
PCT Pub. Date: Nov. 14, 2019

(65) Prior Publication Data
US 2021/0161935 A1     Jun. 3, 2021

Related U.S. Application Data

(60) Provisional application No. 62/669,007, filed on May 9, 2018.

(51) Int. Cl.
| | |
|---|---|
| *A61K 31/7072* | (2006.01) |
| *A61P 31/14* | (2006.01) |
| *A61K 31/4188* | (2006.01) |
| *A61K 31/4439* | (2006.01) |
| *A61K 31/498* | (2006.01) |

(52) U.S. Cl.
CPC ...... *A61K 31/7072* (2013.01); *A61K 31/4188* (2013.01); *A61K 31/4439* (2013.01); *A61K 31/498* (2013.01); *A61P 31/14* (2018.01)

(58) Field of Classification Search
CPC ............ A61K 31/7072; A61K 31/4188; A61K 31/4439; A61K 31/498; A61P 31/14
USPC ........................................................ 514/50
See application file for complete search history.

(56) References Cited

U.S. PATENT DOCUMENTS

| | | | |
|---|---|---|---|
| 6,881,741 B2 | 4/2005 | Chan Chun Kong et al. | |
| 6,887,877 B2 | 5/2005 | Chan Chun Kong et al. | |
| 6,936,629 B2 | 8/2005 | Chan Chun Kong et al. | |
| 7,402,608 B2 | 7/2008 | Chan Chun Kong et al. | |
| 7,569,600 B2 | 8/2009 | Denis et al. | |
| 10,464,914 B2 * | 11/2019 | Jacobson | A61K 31/343 |
| 10,947,210 B2 * | 3/2021 | Jacobson | A61K 45/06 |
| 2017/0014394 A1 | 1/2017 | Roberts et al. | |

FOREIGN PATENT DOCUMENTS

| | | |
|---|---|---|
| WO | WO-02/100846 A1 | 12/2002 |
| WO | WO-02/100851 A2 | 12/2002 |
| WO | WO-2004/052879 A1 | 6/2004 |
| WO | WO-2004/052885 A1 | 6/2004 |
| WO | WO-2006/072347 A2 | 7/2006 |
| WO | WO-2006/119646 A1 | 11/2006 |
| WO | WO-2008/017688 A1 | 2/2008 |
| WO | WO-2008/043791 A2 | 4/2008 |
| WO | WO-2008/058393 A1 | 5/2008 |
| WO | WO-2008/059042 A1 | 5/2008 |
| WO | WO-2008/125599 A1 | 10/2008 |
| WO | WO-2009/000818 A1 | 12/2008 |
| WO | WO-2014/070771 A1 | 5/2014 |
| WO | WO-2015/160907 A2 | 10/2015 |
| WO | WO-2016/154241 A1 | 9/2016 |

OTHER PUBLICATIONS

Glossary of medical education terms, Institute of International Medical Education. http://www.iime.org/glossary.htm Accessed in Mar. 2013. (Year: 2013).*
Aghemo et al. New Horizons in Hepatitis C Antiviral Therapy With Direct-Acting Antivirals. Hepatology 2013;58:428-438. (Year: 2013).*
Amiri et al. HIV, HBV and HCV Coinfection Prevalence in Iran—A Systematic Review and Meta-Analysis. PLoS ONE 11(3): e0151946, 2016. doi:10.1371/journal.pone.0151946 (Year: 2016).*
Berge et al., Pharmaceutical Salts, J. Pharmaceutical Sci., 66(1):1-19 (1977).
Chen et al., The natural history of hepatitis C virus (HCV), Int. J. Med. Sci., 3(2):47-52 (2006).
Cheng et al., In Vitro Antiviral Activity and Resistance Profile Characterization of the Hepatitis C Virus NS5A Inhibitor Ledipasvir, 60(3):1847-1853 (Jan. 2016).
Ghany et al., An update on treatment of genotype 1 chronic hepatitis C virus infection: 2011 practice guideline by the American Association for the Study of Liver Diseases, Hepatology, 54(4):1433-44 (2011).
International Application No. PCT/US2019/031459, International Search Report and Written Opinion, dated Jul. 23, 2019.
Lau et al., Efficacy and safety of 3-week response-guided triple direct-acting antiviral therapy for chronic hepatitis C infection: a phase 2, open-label, proof-of-concept study, Lancet Gastroenterol. Hepatol., 1(2):97-104 (2016).
Poordad et al., Glecaprevir and Pibrentasvir for 12 weeks for Hepatitis C virus genotype 1 infection and prior direct-acting antiviral treatment, Hepatology, 66(2):389-97 (2017).

* cited by examiner

*Primary Examiner* — Yih-Horng Shiao
(74) *Attorney, Agent, or Firm* — MARSHALL, GERSTEIN & BORUN LLP

(57) ABSTRACT

Disclosed herein are combination therapies for use in the treatment or prevention of HCV by administering Compound A and a second HCV inhibitor.

19 Claims, No Drawings

COMBINATION THERAPY FOR TREATMENT OF HCV

BACKGROUND

Hepatitis C virus (HCV) is an enveloped, positive-sense, single-stranded RNA virus, of the genus *Hepacivirus*, belonging to the family Flaviviridae. Infection by HCV is a leading cause of liver disease and cirrhosis in humans. Infection is often asymptomatic, or symptoms are mild, and about 15-20% of infected persons are able to clear the virus without treatment. However, infection in the remaining 80-85% of infected persons develops into persistent infection, which may be life-long, causing liver disease, which can lead to cirrhosis and hepatocellular carcinoma. HCV infection is the most common chronic blood-borne disease in the United States, affecting about 4 million people and causing about 12,000 deaths per year. "Evaluation of Acute Hepatitis C Infection Surveillance—United States, 2008," *MMWR*, Nov. 5, 2010, 59(43). Approximately 170 million persons around the world have chronic hepatitis C infection. Chen et al., *Int J Med Sci*, 2006, 3(2):47-52.

HCV has a simple genome that resides in a single open reading frame of about 9.6 kb. The genome is translated in the infected cell to yield a single polyprotein of about 3000 amino acids, which is then proteolytically processed by host and viral enzymes to produce at least 10 structural and non-structural (NS) proteins—envelope proteins EI and E2, a membrane bound protein p7, and the non-structural proteins NS2, NS3, NS4A, NS4B, NS5A and NS5B. The virus is diversified in infected humans into 16 different antigenically and/or genetically identifiable subtypes or genotypes, some of which are further subdivided into subtypes.

HCV rapidly mutates as it replicates, and is believed to exist as a viral quasispecies, meaning that it mutates rapidly as it replicates to generate many competing genetic varieties of the virus having comparable evolutionary fitness. This intrinsic generation of many varieties in a single infected person makes it very difficult to isolate a single variety for development of a vaccine, and is believed to be associated with the difficulty in developing a vaccine, development of resistance of the virus to specific pharmaceuticals, and persistence of the virus in the host. It is possible that the virus able to develop into immunologically distinct quasispecies under the pressure of the immune response of the host, thereby allowing it to survive and persist.

Approved pharmaceutical treatments include injection of interferon, typically pegylated versions including peginterferon alfa-2a (Pegasys®) or peginterferon alfa-2b (PegIntron®). Clinical use of pegylated interferon was approved by FDA in 2001. Ribavirin (e.g., Ribasphere®, Virazole®, Copegus®, Rebetol®), a guanosine analog that has broad-spectrum activity against viruses, is used to treat HCV infection, but appears not to be effective against HCV when used as a monotherapy. Current standard-of-care therapy includes administering peginterferon in combination with ribavirin. This regimen is limited because of side effects (e.g., flu-like symptoms, leukopenia, thrombocytopenia, depression, and anemia) and only moderate efficacy; success is dependent in part on the genotype predominating in the patient. See Ghany et al., *Hepatology*, 2011, 54(4):1433-44. Typically, hepatitis C was treated with a combination of peg IFN-alfa and ribavirin for a period of 24 or 48 weeks, depending on the HCV genotype. Substantial limitations to efficacy and tolerability remain as many users suffer from side effects, and viral elimination from the body is often incomplete.

The goal of treatment is sustained viral response ("SVR") –meaning that HCV is not measurable in the patient's blood after therapy is completed. SVR12, defined as undetectable HCV RNA 12 weeks post-therapy, is recognized to be essentially a clinical cure. Following treatment with a combination of pegylated interferon alpha and ribavirin, sustained cure rates (sustained viral response) of about 75% or better occur in people with HCV genotypes 2 and 3 in 24 weeks of treatment, about 50% in those with HCV genotype 1 with 48 weeks of treatment, and about 65% in those with HCV genotype 4 in 48 weeks of treatment.

Boceprevir and telaprevir are approved for treating HCV genotype 1 ("GT1"). Both agents are inhibitors of the HCV NS3/4A protease and are used in combination with peg IFN and ribavirin.

Sofosbuvir, an oral uridine nucleotide prodrug inhibitor of NS5B, is approved for the treatment of chronic hepatitis C. For patients infected with HCV GT1 or GT4, the treatment regimen includes sofosbuvir in combination with peg IFN-alfa and ribavirin for a duration of twelve (12) weeks. For patients infected with HCV GT2, the treatment regimen includes sofosbuvir in combination with ribavirin for a duration of twelve (12) weeks. For patients infected with HCV GT3, the treatment regimen includes sofosbuvir in combination with ribavirin for a duration of twenty-four (24) weeks.

A single tablet, an oral combination of sofosbuvir and ledipasvir, a NS5A inhibitor, is approved for patients infected with HCV GT1. For patients without cirrhosis, the treatment regimen includes sofosbuvir in combination with ledipasvir for a duration of twelve (12) weeks. For treatment-experienced patients with cirrhosis, the treatment regimen includes sofosbuvir in combination with ledipasvir for a duration of twenty-four (24) weeks. Additionally, an all oral combination of sofosbuvir (tablet) in combination with simeprevir (capsule), an NS3A/4A protease inhibitor, is approved for patients infected with HCV GT1. For patients without cirrhosis, the treatment regimen includes sofosbuvir in combination with simeprevir for a duration of twelve (12) weeks. For patients with cirrhosis, the treatment regimen includes sofosbuvir in combination with simeprevir for a duration of twenty-four (24) weeks.

A need exists for combination therapies of HCV inhibtiors for treatment of HCV.

SUMMARY

Provided herein are methods of treating or preventing hepatitis C virus (HCV) infection in a subject comprising administering to the subject (1) Compound A or pharmaceutically acceptable salt thereof and (2) a second HCV inhibitor in an amount effective to treat or prevent HCV in the subject. The second HCV inhibtor can comprise one or more inhibitors. In some cases, the second HCV inhibitor comprises a NS5B inhibitor. In some cases, the second HCV inhibitor comprises a NS5A inhibitor. In some cases, the second HCV inhibitor comprises a protease inhibitor. In some cases, the second HCV inhibitor comprises a NS5A and a NS5B inhibitor. NS5A inhibitors, NS5B inhibitors, and protease inhibitors as discussed in detail below.

Also provided herein is a method of treating or preventing hepatitis C virus (HCV) infection in a subject comprising administering to the subject (1) Compound A or pharmaceutically acceptable salt thereof and (2) a combination comprising an HCV NS5A inhibitor and an HCV NS5B inhibitor, in amounts effective to treat or prevent HCV in the subject. In some cases, the HCV NS5A inhibitor comprises daclatasvir, elbasvir, ledipasvir, odalasvir, ombitasvir, pibrentasvir, ravidasvir. ruzasvir, samatasvir, velpatasvir, or a combination thereof, or a pharmaceutically acceptable salt thereof. In various cases, the HCV NS5A inhibitor comprises daclatasvir or velpatasvir, or a pharmaceutically acceptable salt thereof. In some cases, the HCV NS5B inhibitor comprises beclabuvir, dasabuvir, deleobuvir, filibuvir, setrobuvir, sofosbuvir, radalbuvir, uprifosbuvir, or a combination thereof, or a pharmaceutically acceptable salt thereof. In various cases, the HCV NS5B inhibitor is sofosbuvir or a pharmaceutically acceptable salt thereof. In various cases, the combination comprises velpatasvir and sofosbuvir or daclatasvir and sofosbuvir, or a pharmaceutically acceptable salt thereof. In various cases, the method comprises administering to the subject (1) 400 mg of Compound A and (2) a fixed dose combination comprising 100 mg of velpatasvir and 400 mg of sofosbuvir.

Also provided herein is a combination for use in the treatment or prevention of hepatitis C virus (HCV) infection in a subject, comprising (1) Compound A or a pharmaceutically acceptable salt thereof and (2) a combination comprising an HCV NS5A inhibitor and an HCV NS5B inhibitor, in amounts effective to treat or prevent HCV in the subject.

DETAILED DESCRIPTION

Provided herein are methods for the combination therapy for treating or preventing HCV infection in a subject by administration of Compound A or pharmaceutically acceptable salt thereof and a second HCV inhibitor or pharmaceutically acceptable salt thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where a compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where a compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This disclosure also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminium. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

Compound A

Compound A used in the methods disclosed herein is an HCV inhibitor having a structure:

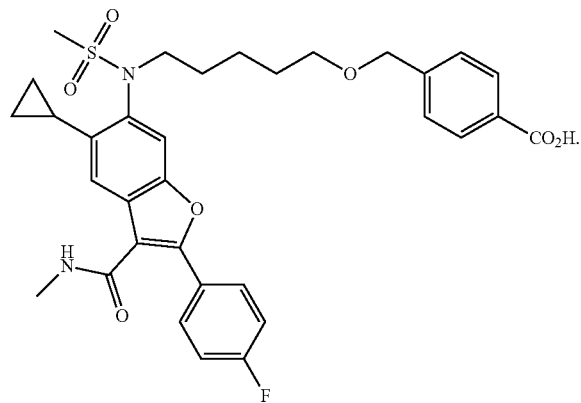 [SMILES: CNC(=O)c1c(-c2ccc(F)cc2)oc2cc(N(CCCCCOCc3ccc(C(=O)O)cc3)S(C)(=O)=O)c(C3CC3)cc12]

Compound A can be as the free acid or can be as a pharmaceutically acceptable salt. The compound can form a base salt with a pharmacologically acceptable cation. Non-limiting examples of such salts include alkali metal or alkaline earth metal salts and, particularly, calcium, magnesium, sodium, lithium, zinc, potassium and iron salts, as well as tetraalkylammonium salts. General information regarding pharmaceutically acceptable salts may be found in Stahl P H, and Wermuth C G, eds., *Handbook of Pharmaceutical Salts: Properties, Selection and Use*, 2002, Wiley-VCH/VHCA Weinheim/Zürich. All weights discussed throughout for Compound A are based upon the free acid compound, not including any salt cation.

The amount of Compound A or salt thereof administered to a subject in the disclosed methods can be in any suitable amount such as, for example, in doses from 0.1 mg/kg to 200 mg/kg body weight, or from 0.25 mg/kg to 100 mg/kg, or from 0.3 mg/kg to 30 mg/kg, based upon weight of free acid of compound. As non-limiting examples, Compound A can be administered in a total daily dose amount from 100 mg to 1000 mg, or from 300 mg to 700 mg, or from 400 mg to 600 mg or any amounts there between. In certain embodiments, the total daily dosage amount for Compound A is 400 mg. In certain embodiments, the total daily dosage amount for Compound A is 600 mg. In some cases, Compound A is administered once per day. In some cases, 400 mg Compound A is administered once per day. In some cases, 600 mg Compound A is administered once per day. In some cases, Compound A is administered twice per day. In some cases, 200 mg Compound A is administered twice per day, for a total daily dose of 400 mg.

Second HCV Inhibitor

The second HCV inhibitor used in the disclosed methods can be any compound, antibody, nucleic acid or protein that inhibits HCV. For example, such HCV inhibitors can be interferons, ribavirin, nucleoside HCV NS5B polymerase inhibitors, non-nucleoside HCV NS5B polymerase inhibitors, HCV NS3-4A protease inhibitors, HCV NS5A inhibitors, HCV entry inhibitors, HCV NS3 inhibitors, HCV NS3 helicase inhibitors, HCV NS4B inhibitors, and/or human cyclophilin inhibitors. When the term "second HCV inhibitor" is used in the singular, unless otherwise noted, it is meant to include both a single second HCV inhibitor or a combination of second HCV inhibitors.

Exemplary interferons include, without limitation, natural, recombinant, and modified (e.g., PEG-linked, albumin-linked) interferon molecules. Interferons include, but are not limited to, interferon alfa-2a (Roferon®), interferon alpha-2b (Intron®), interferon alfacon-1 (Infergen®), peginterferon alfa-2a (Pegasys®) or peginterferon alfa-2b (PegIntron®), recombinant alfa interferon (BLX-883; Locteron®), and albinterferon alfa 2b (Zalbin®). In some cases, the interferon is also administered with ribavirin.

Contemplated NS3-4A protease inhibitors (alternatively referred to as "protease inhibitors") include, without limitation, telaprevir (Incivek™; VX-950; Vertex), boceprevir (Victrelis™; SCH503034; Merck), simeprevir (TMC435; Janssen/Tibotec/Medevir), danoprevir (ITMN-191/RG7227; Hoffmann-La Roche/Genentech), faldaprevir (BI 201335; Boehringer Ingelheim), BI 12202 (Boehringer Ingelheim), vaniprevir (MK-7009; Merck), MK-5172 (Merck), paritaprevir (ABT-450; Abbvie); Glecaprevir (Abbvie), VX500 (Vertex), PHX1766 (Phenomix), BILN2061 (Boehringer Ingelheim), GS-9256 (Gilead), GS-9451 (Gilead), asunaprevir (BMS-650032; Bristol-Myers Squibb), VX-985 (Vertex), sovaprevir (ACH-1625; Achillion), ACH-2684 (Achillion), and narlaprevir (SCH900518; Merck). In some cases, the protease inhibitor is gelcaprevir, grazoprevir, paritaprevir, simeprevir, or voxilaprevir, or a pharmaceutically acceptable salt thereof.

Contemplated NS4B inhibitors include clemizole (Eiger Biopharmaceuticals); and Host-cell entry inhibitors, e.g., ITX5061 (iTherX).

Contemplated cyclophilin inhibitors include cyclophilin-A inhibitors, e.g., Debio 025 (alisporivir), SCY-635, NIM811, and other cyclosporin (ciclosporin) derivatives.

Contemplated NS5A inhibitors include daclatasvir (BMS-790052; Bristol-Myers Squibb), BMS-824383 (Bristol-Myers Squibb), AZD7295 (AstraZeneca), PPI-461 (Presidio), PPI-688 (Presidio), GS-5885 (Gilead), ACH-2928 (Achillion), IDX-719 (Idenix), ombitasvir (ABT-267; Abbvie); ledipasvir (GS-5885; Gilead), ACH-3102 (Achillion), GS-5816 (Gilead), JNJ-56914845 (GSK 2336805; Janssen), MK-8742 (Merck), and pibrentasvir (Abbvie). In some cases, the NS5A inhibitor is daclatasvir, elbasvir, ledipasvir, ombitasvir, pibrentasvir, or velpatasvir, or a pharmaceutically acceptable salt thereof. In some cases, the NS5A inhibitor comprises daclatasvir, elbasvir, ledipasvir, odalasvir, ombitasvir, pibrentasvir, ravidasvir. ruzasvir, samatasvir, velpatasvir, or a combination thereof, or a pharmaceutically acceptable salt thereof. In some cases, the NS5A inhibitor comprises daclatasvir or velpatasvir, or a pharmaceutically acceptable salt thereof.

Inhibitors of NS5B can be classified broadly into three groups: nucleoside analogues (NI), non-nucleoside analogues (NNI), and pyrophosphate compounds (PPi).

Nucleoside analogue compounds (NI), which bind at the enzyme active site and compete with natural nucleoside triphosphates, interfere with viral RNA synthesis. Contemplated nucleoside inhibitors include, but are not limited to, IDX184 (Idenix), mericitabine (RG7128, R-7128, R05024048; Hoffmann-La Roche/Genentech), PSI-7851 (Pharmasset), PSI-938 (Pharmasset), sofosbuvir (SOVALDI®, PSI-7977; Gilead/Pharmasset), TMC647055 (Janssen); and VX-135 (Vertex), as well as phosphoramidate nucleotide analogs such as INX-189 (Inhibitex), TMC649128 (Tibotec/Medevir).

Contemplated NNI compounds include, but are not limited to, JTK-109 (Japan Tobacco), BILB-1941 (Boehringer Ingelheim), MK-3281 (Merck), BI 207127 (Boehringer Ingelheim); filibuvir (PF-868554; Pfizer), VX-759 (VCH- 759; Vertex), VCH-916 (Vertex), VX-222 (VCH-222; Vertex), GS-9669 (Gilead); GSK625433 (Glaxo SmithKline), ANA-598 (Anadys/Roche), dasabuvir (ABT-333; Abbvie), ABT-072 (Abbott), setrobuvir (ANA-5981; Hoffmann-La Roche/Genentech); HCV-796 (ViroPharma/Wyeth), tegobuvir (GS-9190; Gilead), IDX375 (Idenix), filibuvir (Pfizer), tegobuvir (GS 9190; Gilead), VX-222 (Vertex), A-837093 (Abbott), ABT-072 (Abbott), ABT-333 (Abbott), and PF-868554 (Pfizer). Other non-nucleoside inhibitors of NS5B include thiophene-2-carboxylic acids and derivatives thereof (see, e.g., WO 2002/100846, WO 2002/100851, WO 2004/052879, WO 2004/052885, WO 2006/072347, WO 2006/119646, WO 2008/017688, WO 2008/043791, WO 2008/058393, WO 2008/059042, WO 2008/125599, WO 2009/000818, U.S. Pat. Nos. 6,881,741, 7,402,608, 7,569,600, 6,887,877 and U.S. Pat. No. 6,936,629, each of which is incorporated by reference herein).

In some cases, the NS5B inhibitor comprises beclabuvir, dasabuvir, deleobuvir, filibuvir, setrobuvir, sofosbuvir, radalbuvir, uprifosbuvir, or a combination thereof, or a pharmaceutically acceptable salt thereof.

In some cases, the second HCV inhibitor comprises sofosbuvir. Sofosbuvir can be administered in any suitable amount such as, for example, in doses from 0.1 mg/kg to 200 mg/kg body weight, or from 0.25 mg/kg to 100 mg/kg, or from 0.3 mg/kg to 30 mg/kg. As non-limiting examples, sofosbuvir can be administered in a total daily dose amount from 100 mg to 1000 mg, or from 100 mg to 500 mg, or from 200 mg to 400 mg or any amounts there between. In certain embodiments, the total daily dosage amount for sofosbuvir is 200 mg. In certain embodiments, the total daily dosage amount for sofosbuvir is 400 mg. In some cases, sofosbuvir is administered once per day. In some cases, 400 mg sofosbuvir is administered once per day.

In some cases, the second HCV inhibitor comprises velpatasvir. Velpatasvir can be administered in any suitable amount such as, for example, in doses from 0.1 mg/kg to 200 mg/kg body weight, or from 0.25 mg/kg to 100 mg/kg, or from 0.3 mg/kg to 30 mg/kg. As non-limiting examples, velpatasvir can be administered in a total daily dose amount from 50 mg to 500 mg, or from 50 mg to 200 mg, or from 50 mg to 100 mg or any amounts there between. In certain embodiments, the total daily dosage amount for velpatasvir is 100 mg. In some cases, velpatasvir is administered once per day. In some cases, 100 mg velpatasvir is administered once per day.

In some cases, the second HCV inhibitor comprises ledipasvir. Ledipasvir can be administered in any suitable amount such as, for example, in doses from 0.1 mg/kg to 200 mg/kg body weight, or from 0.25 mg/kg to 100 mg/kg, or from 0.3 mg/kg to 30 mg/kg. As non-limiting examples, ledipasvir can be administered in a total daily dose amount from 50 mg to 500 mg, or from 50 mg to 200 mg, or from 50 mg to 100 mg or any amounts there between. In certain embodiments, the total daily dosage amount for ledipasvir is 90 mg. In some cases, ledipasvir is administered once per day. In some cases, 90 mg ledipasvir is administered once per day.

In some cases, the second HCV inhibitor comprises pibrentasvir. Pibrentasvir can be administered in any suitable amount such as, for example, in doses from 0.1 mg/kg to 200 mg/kg body weight, or from 0.25 mg/kg to 100 mg/kg, or from 0.3 mg/kg to 30 mg/kg. As non-limiting examples, pibrentasvir can be administered in a total daily dose amount from 50 mg to 500 mg, or from 50 mg to 200 mg, or from 100 mg to 150 mg or any amounts there between. In certain embodiments, the total daily dosage amount for pibrentasvir is 120 mg. In some cases, pibrentasvir is administered once per day. In some cases, 120 mg pibrentasvir is administered once per day.

In some cases, the second HCV inhibitor comprises glecaprevir. Glecaprevir can be administered in any suitable amount such as, for example, in doses from 0.1 mg/kg to 200 mg/kg body weight, or from 0.25 mg/kg to 100 mg/kg, or from 0.3 mg/kg to 30 mg/kg. As non-limiting examples, glecaprevir can be administered in a total daily dose amount from 100 mg to 1000 mg, or from 100 mg to 500 mg, or from 200 mg to 400 mg or any amounts there between. In certain embodiments, the total daily dosage amount for glecaprevir is 200 mg. In certain embodiments, the total daily dosage amount for glecaprevir is 300 mg. In some cases, glecaprevir is administered once per day. In some cases, 300 mg glecaprevir is administered once per day.

In some cases, the second HCV inhibitor comprises Compound B, which has a structure of

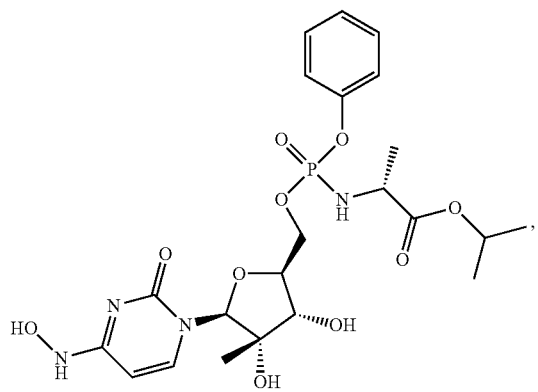 [SMILES: CC(C)OC(=O)[C@@H](C)NP(=O)(OC[C@@H]1O[C@H](n2ccc(NO)nc2=O)[C@@](C)(O)[C@H]1O)Oc1ccccc1]

or pharmaceutically acceptable salt thereof. In some cases, the second HCV inhibitor comprises Compound C, which has a structure of

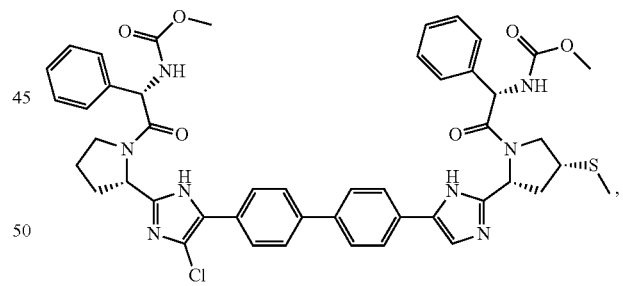

or pharmaceutically acceptable salt thereof.

Any of Compound B and C can be administered in any suitable amount such as, for example, in doses from 0.1 mg/kg to 200 mg/kg body weight, or from 0.25 mg/kg to 100 mg/kg, or from 0.3 mg/kg to 30 mg/kg, based upon weight of free acid or base of compound. As non-limiting examples, Compound B or C can be administered in a total daily dose amount from 100 mg to 1000 mg, or from 300 mg to 700 mg, or from 400 mg to 600 mg or any amounts there between. In certain embodiments, the total daily dosage amount for Compound B or C is 400 mg. In certain embodiments, the total daily dosage amount for Compound B or C is 600 mg. In some cases, Compound B or C is administered once per day. In some cases, 400 mg Compound B or C is administered once per day. In some cases, 600 mg Compound B or C is administered once per day. In some cases, Compound B or C is administered twice per day. In some cases, 200 mg Compound B or C is administered twice per day, for a total daily dose of 400 mg.

In some cases, the second HCV inhibitor comprises daclatasvir, or a pharmaceutically acceptable salt thereof. Daclatasvir can be administered in any suitable amount such as, for example, in doses from 0.1 mg/kg to 200 mg/kg body weight, or from 0.25 mg/kg to 100 mg/kg, or from 0.3 mg/kg to 30 mg/kg. As non-limiting examples, daclatasvir can be administered in a total daily dose amount from 30 mg to 300 mg, or from 30 mg to 200 mg, or from 30 mg to 80 mg or any amounts there between. In certain embodiments, the total daily dosage amount for daclatasvir is 60 mg. In some cases, daclatasvir is administered once per day. In some cases, 60 mg daclatasvir is administered once per day.

In some cases, the second HCV inhibitor comprises asunaprevir, or a pharmaceutically acceptable salt thereof. Asunaprevir can be administered in any suitable amount such as, for example, in doses from 0.1 mg/kg to 200 mg/kg body weight, or from 0.25 mg/kg to 100 mg/kg, or from 0.3 mg/kg to 30 mg/kg. As non-limiting examples, asunaprevir can be administered in a total daily dose amount from 100 mg to 1000 mg, or from 100 mg to 500 mg, or from 100 mg to 300 mg or any amounts there between. In certain embodiments, the total daily dosage amount for asunaprevir is 200 mg. In some cases, asunaprevir is administered twice per day. In some cases, 100 mg asunaprevir is administered twice per day, for a total daily dose of 200 mg.

In some cases, the second HCV inhibitor comprises simeprevir, or a pharmaceutically acceptable salt thereof. Simeprevir can be administered in any suitable amount such as, for example, in doses from 0.1 mg/kg to 200 mg/kg body weight, or from 0.25 mg/kg to 100 mg/kg, or from 0.3 mg/kg to 30 mg/kg. As non-limiting examples, simeprevir can be administered in a total daily dose amount from 50 mg to 500 mg, or from 50 mg to 200 mg, or from 100 mg to 200 mg or any amounts there between. In certain embodiments, the total daily dosage amount for simeprevir is 150 mg. In some cases, simeprevir is administered once per day. In some cases, 150 mg simeprevir is administered once per day.

In some cases, the second HCV inhibitor comprises ribavirin, or a pharmaceutically acceptable salt thereof. Ribavirin may include any suitable form or formulation of ribavirin. Exemplary formulations of ribavirin include COPEGUS®, REBETOL® and RIBASPHERE®. An exemplary pro-drug of ribavirin is taribavirin having the chemical name of 1-β-D-ribofuranosyl-l,2,4-triazole-3-carboxamidine. Ribavirin and taribavirin may be administered in accordance with ribavirin and taribavirin administration well known in the art. In some embodiments, COPEGUS® or REBETOL® is administered in a daily dosage amount from 500 mg to 1500 mg in one dose or in divided doses. In some embodiments, COPEGUS® or REBETOL® is administered in a daily dosage amount of 800 mg. In some embodiments, REBETOL® is administered in a daily dosage amount of 1000 mg. In some embodiments, COPEGUS® or REBETOL® is administered in a daily dosage amount of 1200 mg. In some embodiments, REBETOL® is administered in a daily dosage amount of 1400 mg. Suitable dosages of ribavirin are dependent on the weight of the subject, for example 1000-1200 mg. Suitable total daily dosages of ribavirin include, but are not limited to 400 mg to 1400 mg a day, alternatively 800 mg to 1400 mg per day, alternatively 400 mg to 1200 mg, alternatively 800 mg to 1200 mg.

In some cases, the second HCV inhibitor comprises a NS5B inhibitor and a NS5A inhibitor. In some specific instances of these cases, the NS5B inhibitor is a nucleoside inhibitor. In some specific instances of these cases, the NS5B inhibitor comprises sofosbuvir or pharmaceutically acceptable salt thereof. In some specific instances of these cases, the NS5A inhibitor comprises velpatasvir or pharmaceutically acceptable salt thereof. In some specific instances of these cases, the NS5A inhibitor comprises ledipasvir or pharmaceutically acceptable salt thereof. In some cases, the NS5A inhibitor comprises velpatasvir and the NS5B inhibitor comprises sofosbuvir, or a pharmaceutically acceptable salt thereof. In some cases, the NS5A inhibitor comprises daclatasvir and the NS5B inhibitor comprises sofosbuvir, or a pharmaceutically acceptable salt thereof. In some instances, the subject is administered 400 mg of Compound A and a fixed dose combination comprising 100 mg of velpatasvir and 400 mg of sofosbuvir.

In some cases, the second HCV inhibitor comprises a NS5A inhibitor and a protease inhibitor. In some specific instances of these cases, the NS5A inhibitor comprises pibrentasvir or pharmaceutically acceptable salt thereof. In some specific instances of these cases, the protease inhibitor comprises glecaprevir, or pharmaceutically acceptable salt thereof.

In some cases, the second HCV inhibitor comprises a NS5A inhibitor, a NS5B inhibitor, and a protease inhibitor. In some specific instances of these cases, the NS5B inhibitor is a nucleoside inhibitor. In some specific instances of these cases, the NS5B inhibitor comprises sofosbuvir or pharmaceutically acceptable salt thereof. In some specific instances of these cases, the NS5A inhibitor comprises velpatasvir or pharmaceutically acceptable salt thereof. In some specific instances of these cases, the NS5A inhibitor comprises ledipasvir or pharmaceutically acceptable salt thereof. In some specific instances of these cases, the NS5A inhibitor comprises pibrentasvir or pharmaceutically acceptable salt thereof. In some specific instances of these cases, the protease inhibitor comprises glecaprevir, or pharmaceutically acceptable salt thereof.

Combination Therapy for HCV Infections

The methods disclosed herein contemplate using any of the combination of HCV inhibitors to treat HCV infection. The method comprises administering an effective amount of such a combination to an HCV patient in need thereof. In some embodiments, the patient is infected with HCV genotype 1. In other embodiments, the patient is infected with HCV genotype 2. In yet other embodiments, the patient is infected with HCV genotype 3. In yet other embodiments, the patient is infected with HCV genotype 4. In yet other embodiments, the patient is infected with HCV genotype 5. In yet other embodiments, the patient is infected with HCV genotype 6.

In some cases, the patient is a HCV-treatment naive patient, a HCV-treatment experienced patient, an interferon non-responder (e.g., a null responder), or not a candidate for interferon treatment. As used in this application, the interferon non-responder patients include partial interferon responders and interferon rebound patients. See GUIDANCE FOR INDUSTRY—CHRONIC HEPATITIS C VIRUS INFECTION: DEVELOPING DIRECT-ACTING ANTIVIRAL AGENTS FOR TREATMENT (FDA, September 2010, draft guidance) for the definitions of naive, partial responder, responder relapser (i.e., rebound), and null responder patients. The interferon non-responder patients also include null responder patients. In any method described herein, the patient being treated can be a treatment-naive patient.

In any method described herein, the patient being treated can be an interferon non-responder. In any method described herein, the patient being treated can be an interferon null-responder. In any method described herein, the patient being treated can be without cirrhosis. In any method described herein, the patient being treated can be a cirrhotic patient. In any method described herein, the patient being treated can be a patient with compensated cirrhosis.

The disclosed combination therapy generally constitutes a complete treatment regimen, and in some embodiments, no subsequent regimen is intended (e.g., no subsequent interferon regimen). Thus, in some cases, a treatment or use described herein does not include any subsequent treatment. Preferably, a treatment or use described herein does not include any subsequent interferon- and/or ribavirin-containing treatment.

In certain embodiments, Compound A and the additional HCV inhibitor or inhibitors can be administered in a substantially simultaneous manner (e.g., within about 5 min of each other), in a sequential manner, or both. It is contemplated that such combination therapies can include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. In some cases, Compound A and the additional HCV inhibitor or inhibitors are administered sequentially and within 30 minutes, 60 minutes, 2 hours, 4 hours, 6 hours, 8 hours, 10 hours, 12 hours, 18 hours, 24 hours, 36 hours, or 48 hours of each other. In some case, Compound A is administered before the additional HCV inhibitor or inhibitors, while in others, Compound A is administered after the additional HCV inhibitor or inhibitors. In some cases, Compound A and the additional HCV inhibitor or inhibitors are administered substantially simultaneously and within 10 minutes, 5 minutes, or 1 minute of each other. In various cases, Compound A and the additional HCV inhibitor or inhibitors are administered according to different dosing schedules—e.g., one therapeutic is administered once a day, while the other is administered twice a day. In some cases, Compound A and the additional HCV inhibitor or inhibitors are administered according to the same dosing schedules. In some specific cases, each therapeutic is administered once a day.

The present disclosure is also directed, in part, to pharmaceutical compositions comprising Compound A and the additional HCV inhibitor or inhibitors for use in the disclosed combinations. For example, combination therapies provided herein include pharmaceutical compositions comprising Compound A, sofosbuvir, and velpatasvir or ledipasvir, or pharmaceutically acceptable salts thereof. Combination therapies provided herein also include pharmaceutical compositions comprising Compound A, glecaprevir, and/or pibrentasvir, or pharmaceutically acceptable salts thereof. In some cases, combination therapies provided herein comprise Compound A, glecaprevir, and pibrentasvir. In some cases, the combination therapies comprise a fixed dose combination of Compound A, 100 mg of glecaprevir, and 40 mg of pibrentasvir. In some cases, combination therapies provided herein comprise Compound A, velpatasvir, and sofosbuvir. In some cases, the combination therapies comprise a fixed dose combination of Compound A, 100 mg of velpatasvir, and 400 mg of sofosbuvir.

Compound A and the additional HCV inhibitor or inhibitors can be administered for any suitable period such as at least 4 weeks, at least 6 weeks, or at least 8 weeks. In certain embodiments, the combination therapy is administered for not more than 24 weeks. In certain embodiments, the combination therapy is administered for not more than 12 weeks. In certain embodiments, the combination therapy is administered for not more than 8 weeks. In certain embodiments, the combination therapy is administered for not more than 6 weeks.

Oftentimes, combination therapies fail to improve the therapeutic effect on the subject in need over what each therapeutic alone would achieve, or only moderately improve the therapeutic effect over either therapeutic alone. However, the methods disclosed herein to the use of a combination therapy can result in inhibition of HCV that is additive, compared to the inhibition of each therapeutic alone. Thus, the combination therapy results in a therapeutic effect that is greater than the individual effect of either therapeutic agent alone. For example, a combination therapy disclosed herein can have an additive effect that is at least 10% improved therapeutic effect over the therapeutic effect of one of the therapeutic agents (e.g., Compound A) alone. In some cases, the additive effect is an at least 15%, at least 20%, at least 25%, at least 30%, at least 35%, at least 40%, at least 50%, at least 60% improvement over one of the therapeutic agents (e.g., Compound A) alone.

In some cases, the results are synergistic, compared to the inhibition of each therapeutic alone. Thus, the combination therapy results in a therapeutic effect that is greater than the sum of the individual effects of each therapeutic agent. In some cases, the synergistic effect is an at least 15%, at least 20%, at least 25%, at least 30%, at least 35%, at least 40%, at least 50%, at least 60% improvement over the sum of the therapeutic agents.

In some cases, the activity of the disclosed combination therapy is such that the treatment can be administered for less time than either component of the combination therapy alone.

Measurement of synergy and/or additive results of the combination therapy as disclosed herein can be performed in view of the assay described in the examples provided below.

Various measures can be used to express the effectiveness of a method disclosed herein. One such measure is SVR, which, as used herein, means that the virus is undetectable at the end of therapy and for at least 6 weeks after the end of therapy (SVR6); for at least 8 weeks after the end of therapy (SVR8); preferably, the virus is undetectable at the end of therapy and for at least 12 weeks after the end of therapy (SVR12); more preferably, the virus is undetectable at the end of therapy and for at least 16 weeks after the end of therapy (SVR 16); and highly preferably, the virus is undetectable at the end of therapy and for at least 24 weeks after the end of therapy (SVR24). SVR24 is often considered as a functional definition of cure; and a high rate of SVR at less than 24 week post-treatment (e.g., SVR8 or SVR12) can be predictive of a high rate of SVR24.

The disclosure will be more fully understood by reference to the following examples which detail exemplary embodiments. They should not, however, be construed as limiting the scope of the disclosure. All citations throughout the disclosure are hereby expressly incorporated by reference.

EXAMPLES

Materials: Cells—The HCV GT1b (Con1, HCV-1b) replicon cells were generated and provided by WuXi AppTec.

The HCV-1b replicon cells are Huh7 cells stably transfected with the HCV GT1b replicon containing the HCV subgenome, resistance selection gene NEO and reporter gene firefly luciferase.

Compounds—Test compounds were prepared according to previously disclosed synthesis or were purchased from commercial sources.

Reagents—The main reagents used were Dulbecco's Minimal Essential Medium (DMEM); Fetal bovine serum (FBS); GlutaMax; Geneticin selective antibiotic (G418); Penicillin-Streptomycin; MEM non-essential amino acids; Dulbecco's Phosphate Buffered Saline (DPBS); 0.05% Trypsin-EDTA; Dimethyl sulfoxide (DMSO); Bright-Glo; and CellTiter-Fluor.

Equipment—The major equipment used were the Automated Liquid Workstation (Labcyte, Echo555) and Microplate Reader Envision (Perkin Elmer, 2104).

Software—HCV replicon data was analyzed using MacSynergy™ II software.

Methods: This study was to assess combination effects of the Compound A with other HCV antivirals on HCV replicon replication in the HCV GT1b replicon assay.

The 2-drug combination experiment was designed using a checkboard cross pattern of 7 drug concentrations of each agent, including each agent alone, in triplicate, plated with the Automated Liquid Workstation (Labcyte, Echo555). The concentrations of the test compounds were 0.125, 0.25, 0.5, 1, 2, 4, 8× $EC_{50}$ values. The $EC_{50}$ values of the test compounds were determined in a separate HCV GT1b replicon assay. The regimens of the compound combinations are listed in Table 1—where each regimen includes Compound A as the first compound. The test concentrations of the compounds are as shown in the tables below. The final concentration of DMSO in the cell culture medium was 0.5%.

TABLE 1

| Regimen | Second Inhibitor Drug class |
|---|---|
| 1 | Sofosbuvir NS5B Nucleoside inhibitor |
| 2 | Compound B NS5B Nucleoside inhibitor |
| 3 | Ledipasvir NS5A inhibitor |
| 4 | Compound C NS5A inhibitor |
| 5 | Velpatasvir NS5A inhibitor |
| 6 | Pibrentasvir NS5A inhibitor |
| 7 | Daclatasvir NS5A inhibitor |
| 8 | Asunaprevir NS3 protease inhibitor |
| 9 | Glecaprevir NS3 protease inhibitor |
| 10 | Simeprevir NS3 protease inhibitor |
| 11 | Ribavirin Guanine analog |

The HCV-1b cells were seeded at a density of 8,000 cells per well in 96-well plates and cultured in DMEM containing 10% FBS at 5% $CO_2$ and 37° C. The replicon cells were treated with the compounds for 3 days.

Cell viability was assessed with CellTiter-Fluor in accordance with the protocol provided by the supplier. The CellTiter-Fluor reagent was added to the wells and incubated at 5% $CO_2$ and 37° C. for 1 h. The fluorimetric signal was measured with an Envision (Perkin Elmer, USA). The raw fluorimetric signal data (RFU) was used to calculate the cell viability using the equation:

$$\%\text{Viability} = \frac{CPD - HPE}{ZPE - HPE} \times 100,$$

where CPD is the signal from a well containing a test compound; HPE is the average of signals from medium wells; and ZPE is the average of signals from DMSO control wells.

The antiviral activity of the compounds was determined by monitoring activity of the replicon reporter firefly luciferase using Bright Glo in accordance with the protocol provided by the supplier. The combination indices were calculated using the MacSynergy™ II software. A positive combination index value indicates synergism, and a negative combination index value indicates antagonism.

All combination regimens examined did not show obvious cytotoxicity at tested concentrations. As shown in the tables below, Compound A showed either additive or synergistic effect with HCV NS5B nucleoside inhibitors, NS5A inhibitors, NS3 protease inhibitors, NS3 helicase inhibitors, and ribavirin in HCV replicon cell-based assays.

TABLE 2

Compound A Combination with NS5B Nucleoside Inhibitor

| $2^{nd}$ Inhibitor | Synergy volume | Antagonism volume | Combination regimen effect |
|---|---|---|---|
| Sofosbuvir | 9.47 | 0.00 | Additive |
| Compound B | 3.30 | 0.00 | Additive |

TABLE 3

Compound A Combination with NS5A Inhibitor

| $2^{nd}$ Inhibitor | Synergy volume | Antagonism volume | Combination regimen effect |
|---|---|---|---|
| Ledipasvir | 38.55 | −1.08 | Minor synergy |
| Compound C | 3.57 | 0 | Additive |
| Velpatasvir | 0.76 | −7.92 | Additive |
| Pibrentasvir | 5.7 | −24.59 | Additive |
| Daclatasvir | 33.47 | −3.05 | Minor synergy |

TABLE 4

Compound A Combination with NS3 Protease Inhibitor

| $2^{nd}$ Inhibitor | Synergy volume | Antagonism volume | Combination regimen effect |
|---|---|---|---|
| Asunaprevir | 4.9 | −1.32 | Additive |
| Glecaprevir | 47.37 | 0.00 | Minor synergism |
| Simprevir | 13.39 | 0.00 | Additive |
| Ribavirin | 0.24 | −9.76 | Additive |

TABLE 5

Comparator Combination Regimens

| 1st Inhibitor | 2nd Inhibitor | Synergy volume | Antagonism volume | Combination effect |
|---|---|---|---|---|
| Glecaprevir | Pibrentasvir | 0.27 | −5.73 | Additive |
| Velpatasvir | Sofosbuvir | 34 | −18 | Minor synergism |

What is claimed:

1. A method of treating hepatitis C virus (HCV) infection in a subject in need thereof comprising administering to the subject (1) a first therapeutic selected from the group consisting of Compound A and a pharmaceutically acceptable salt thereof:

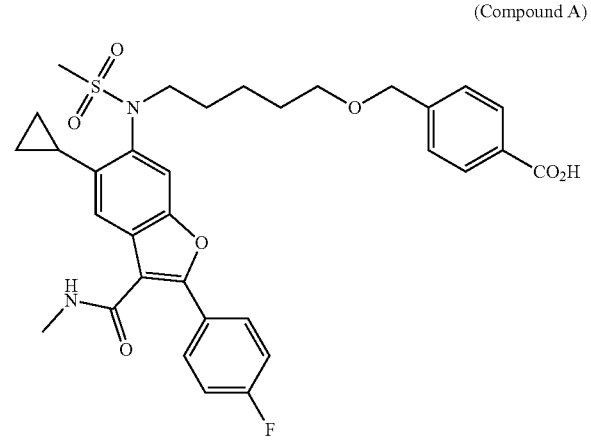 [SMILES: CNC(=O)c1c(-c2ccc(F)cc2)oc2cc(N(CCCCCOCc3ccc(C(=O)O)cc3)S(C)(=O)=O)c(C3CC3)cc12]

(Compound A)

and (2) a second therapeutic selected from an NS5B inhibitor and/or an NS5A inhibitor, and optionally a third therapeutic selected from the group consisting of an NS3A/4A protease inhibitor and ribavirin in amounts effective to treat HCV in the subject.

2. The method of claim 1, wherein:
   (i) the NS5B inhibitor is sofosbuvir or a pharmaceutically acceptable salt thereof; or
   (ii) the NS5A inhibitor is velpatasvir or a pharmaceutically acceptable salt thereof.

3. The method of claim 1, wherein the second therapeutic or third therapeutic is selected from the group consisting of:
   (i) each of sofosbuvir and velpatasvir, or a pharmaceutically acceptable salt thereof;
   (ii) ledipasvir, or a pharmaceutically acceptable salt thereof;
   (iii) each of sofosbuvir and ledipasvir, or a pharmaceutically acceptable salt thereof;
   (iv) pibrentasvir, or a pharmaceutically acceptable salt thereof;
   (v) glecaprevir, or a pharmaceutically acceptable salt thereof;
   (vi) each of pibrentasvir and glecaprevir, or pharmaceutically acceptable salts thereof;
   (vii) Compound B, or a pharmaceutically acceptable salt thereof:

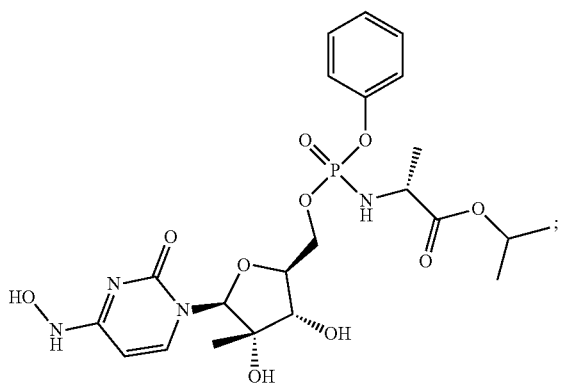

(Compound B)

(viii) Compound C, or a pharmaceutically acceptable salt thereof:

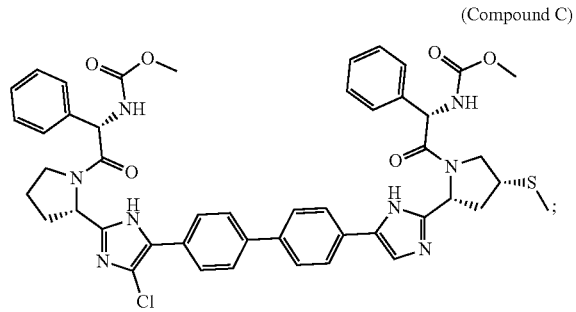 [SMILES: COC(=O)N[C@H](C(=O)N1C[C@H](SC)C[C@@H]1c1ncc(-c2ccc(-c3ccc(-c4[nH]c([C@@H]5CCCN5C(=O)[C@@H](NC(=O)OC)c5ccccc5)nc4Cl)cc3)cc2)[nH]1)c1ccccc1]

(Compound C)

(ix) daclatasvir, or a pharmaceutically acceptable salt thereof;
(x) asunaprevir, or a pharmaceutically acceptable salt thereof;
(xi) simeprevir, or a pharmaceutically acceptable salt thereof;
(xii) ribavirin, or a pharmaceutically acceptable salt thereof;
(xiii) grazoprevir, or a pharmaceutically acceptable salt thereof;
(xiv) paritaprevir, or a pharmaceutically acceptable salt thereof;
(xv) voxilaprevir, or a pharmaceutically acceptable salt thereof;
(xvi) elbasvir, or a pharmaceutically acceptable salt thereof;
(xvii) ombitasvir, or a pharmaceutically acceptable salt thereof;
(xviii) dasabuvir, or a pharmaceutically acceptable salt thereof, and combinations thereof.

4. The method of claim 1, wherein Compound A or salt thereof is co-formulated with the second therapeutic.

5. The method of claim 1, wherein the subject is a non-responder.

6. The method of claim 5, wherein the second therapeutic is an NS5A inhibitor, and the third therapeutic is the protease inhibitor.

7. The method of claim 6, wherein the second therapeutic further comprises an NS5B inhibitor.

8. A method of treating hepatitis C virus (HCV) infection in a subject in need thereof comprising administering to the subject (1) a first therapeutic selected from the group consisting of Compound A:

(Compound A)

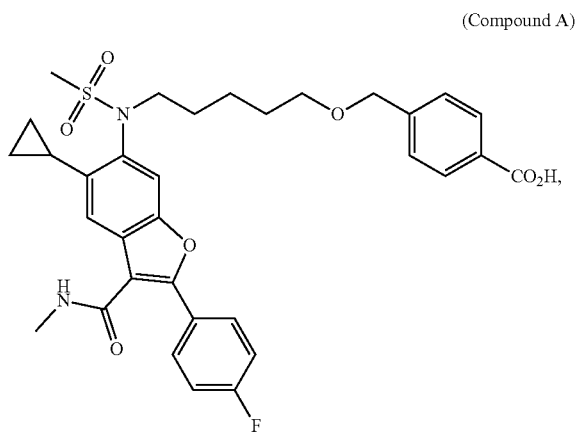 [SMILES: CNC(=O)c1c(-c2ccc(F)cc2)oc2cc(N(CCCCCOCc3ccc(C(=O)O)cc3)S(C)(=O)=O)c(C3CC3)cc12]

(Compound A)

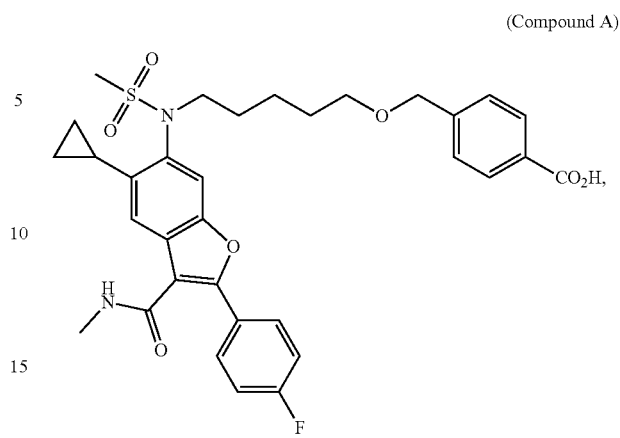

and a pharmaceutically acceptable salt thereof and (2) a second therapeutic selected from a combination of an HCV NS5A inhibitor and an HCV NS5B inhibitor, in amounts effective to treat HCV in the subject.

9. The method of claim 8, wherein the HCV NS5A inhibitor is selected from the group consisting of daclatasvir, elbasvir, ledipasvir, odalasvir, ombitasvir, pibrentasvir, ravidasvir, ruzasvir, samatasvir, velpatasvir, a pharmaceutically acceptable salt thereof, and a combination thereof.

10. The method of claim 8, wherein the HCV NS5B inhibitor, is selected from the group consisting of beclabuvir, dasabuvir, deleobuvir, filibuvir, setrobuvir, sofosbuvir, radalbuvir, uprifosbuvir, a pharmaceutically acceptable salt thereof, and a combination thereof.

11. The method of claim 8, wherein the second therapeutic is selected from the group consisting of the combination of velpatasvir and sofosbuvir, the combination of daclatasvir and sofosbuvir, and pharmaceutically acceptable salts thereof.

12. The method of claim 11, wherein the method comprises administering to the subject (1) 400 mg of Compound A and (2) a fixed dose combination of 100 mg of velpatasvir and 400 mg of sofosbuvir.

13. A method of treating hepatitis C virus (HCV) infection in a subject in need thereof comprising administering to the subject (1) a first therapeutic selected from Compound A:

(Compound A), or a pharmaceutically acceptable salt thereof, and a second therapeutic selected from the group consisting of (2) a combination of glecaprevir and pibrentasvir and (3) a combination of velpatasvir and sofosbuvir, in amounts effective to treat HCV in the subject.

14. The method of claim 13, wherein the method comprises administering to the subject a fixed dose combination of:
   (i) 100 mg of glecaprevir and 40 mg of pibrentasvir; or
   (ii) 100 mg of velpatasvir and 400 mg of sofosbuvir.

15. The method of claim 1, wherein Compound A and the second therapeutic and optionally an NS3A/4A protease inhibitor or ribavirin are administered for four to eight weeks.

16. The method of claim 1, wherein Compound A or salt thereof is administered at a total daily dose of 400 to 600 mg/day.

17. The method of claim 1, wherein Compound A or salt thereof is administered once per day or twice per day.

18. The method of claim 1, wherein the subject suffers from HCV genotype 1, HCV genotype 2, HCV genotype 3, HCV genotype 4, HCV genotype 5, or HCV genotype 6.

19. The method of claim 1, wherein the subject is co-infected with HIV, HBV, or both HIV and HBV.

* * * * *

UNITED STATES PATENT AND TRADEMARK OFFICE
CERTIFICATE OF CORRECTION

| | |
|---|---|
| PATENT NO. | : 11,752,166 B2 |
| APPLICATION NO. | : 17/047209 |
| DATED | : September 12, 2023 |
| INVENTOR(S) | : Irina C. Jacobson et al. |

It is certified that error appears in the above-identified patent and that said Letters Patent is hereby corrected as shown below:

In the Claims

At Column 17, Line 30, "inhibitor," should be -- inhibitor --.

At Column 18, Line 20, "(Compound A), or" should be -- or --.

Signed and Sealed this
Second Day of April, 2024

Katherine Kelly Vidal
*Director of the United States Patent and Trademark Office*